United States Patent
Kim et al.

(10) Patent No.: US 6,838,280 B2
(45) Date of Patent: Jan. 4, 2005

(54) CONSTRUCTION OF HIGH EFFICIENCY RETROVIRAL VECTOR FOR GENE THERAPY OF HUNTER SYNDROME

(75) Inventors: Sunyoung Kim, Seoul (KR); Seung Shin Yu, Seoul (KR); Youngtae Hong, Seoul (KR); Jong-Mook Kim, Seoul (KR); Eun Young Han, Seoul (KR)

(73) Assignee: ViroMed Limited (KR)

( * ) Notice: Subject to any disclaimer, the term of this patent is extended or adjusted under 35 U.S.C. 154(b) by 0 days.

(21) Appl. No.: 10/375,190

(22) Filed: Feb. 25, 2003

(65) Prior Publication Data

US 2003/0165469 A1 Sep. 4, 2003

Related U.S. Application Data

(60) Provisional application No. 60/360,062, filed on Feb. 25, 2002.

(51) Int. Cl.[7] .......................... C12N 15/00; C12N 15/86
(52) U.S. Cl. ..................................... 435/320.1; 435/456
(58) Field of Search .............................. 435/320.1, 456, 435/372; 424/93.21

(56) References Cited

PUBLICATIONS

Romano et al. Latest developments in gene transfer technology: Achievements, perspectives, and controversies over therapeutic applications. Stem cells 18:19–39, 2000.*
McIvor, R.S. Gene therapy of genetic diseases and cancer. Pediatr. Transplantation. vol. 3, suppl. 1, pp. 116–121, 1999.*
Dang et al. Gene therapy and transiational cancer research. Clin. Cancer Res. 5:471–474, 1999.*
Kim et al. Construction of retroviral vectors with improved safety, gene expression, and versatility. J. Virol. 72:994–1004, 1998.*

* cited by examiner

*Primary Examiner*—David Guzo
*Assistant Examiner*—Quang Nguyen
(74) *Attorney, Agent, or Firm*—Anderson Kill & Olick, PC (57) ABSTRACT

The present invention provides a retroviral vector containing an iduronate-2-sulfatase (IDS) gene but without selective marker gene, constructed on, as a backbone, a minimum sized MLV-based retroviral vector which does not contain any viral coding sequences but can still produce a high viral titer and drive a high level of gene expression.

1 Claim, 4 Drawing Sheets

A. Transient Transduction Assay with Same Volume of Viral Vector

B. Transient Transduction with Same Amount of Viral Vector

FIG. 4

A. Northern Hybridization

Actin →

Relative Intensity    0    3.02   3.59   1.0   10.5

B. Quantitation of IDS mRNA in transduced cells by using Quantitative real time PCR

| Vector | C_T Value | Relative Induction Fold of IDS mRNA Expression |
|---|---|---|
| Untransduced Cells | 22.412 | |
| L-IDS-SN | 18.057 | 1.54 |
| MIN-IDS | 17.837 | 1.79 |
| MIM-IDS | 18.682 | 1 |
| MT-IDS | 16.407 | 4.84 |
| No Template Control | 40 | |

FIG. 5

SEQUENCE LISTING

<160> NUMBER OF SEQ ID NOS: 8

<210> SEQ ID NO 1
<211> LENGTH: 42
<212> TYPE: DNA
<213> ORGANISM: Artificial Sequence
<220> FEATURE:
<223> OTHER INFORMATION: IDS5

<400> SEQUENCE: 1
gtcgacgcta gcatgccgcc accccggacc ggccgaggcc tt        42

<210> SEQ ID NO 2
<211> LENGTH: 38
<212> TYPE: DNA
<213> ORGANISM: Artificial Sequence
<220> FEATURE:
<223> OTHER INFORMATION: IDS3

<400> SEQUENCE: 2
gcggccgctc aaggcatcaa caactggaaa agatctcc             38

<210> SEQ ID NO 3
<211> LENGTH: 18
<212> TYPE: DNA
<213> ORGANISM: Artificial Sequence
<220> FEATURE:
<223> OTHER INFORMATION: PRIMER FOR ONE-STEP RT-PCR

<400> SEQUENCE: 3
cccacagcct cctcttcc                                   18

<210> SEQ ID NO 4
<211> LENGTH: 22
<212> TYPE: DNA
<213> ORGANISM: Artificial Sequence
<220> FEATURE:
<223> OTHER INFORMATION: PRIMER FOR ONE-STEP RT-PCR

<400> SEQUENCE: 4
tctcctgcca gtgaggaaag aa                              22

<210> SEQ ID NO 5
<211> LENGTH: 20
<212> TYPE: DNA
<213> ORGANISM: Artificial Sequence
<220> FEATURE:
<223> OTHER INFORMATION: PRIMER FOR REAL-TIME QUANTITATIVE PCR

<400> SEQUENCE: 5
gtaacgccat tttgcaaggc                                 20

<210> SEQ ID NO 6
<211> LENGTH: 21
<212> TYPE: DNA
<213> ORGANISM: Artificial Sequence
<220> FEATURE:
<223> OTHER INFORMATION: PRIMER FOR REAL-TIME QUANTITATIVE PCR

<400> SEQUENCE: 6
accacaagtc ggatgcaact g                               21

<210> SEQ ID NO 7
<211> LENGTH: 21
<212> TYPE: DNA
<213> ORGANISM: Artificial Sequence
<220> FEATURE:
<223> OTHER INFORMATION: PRIMER FOR PCR

<400> SEQUENCE: 7
cttctctggc tgggtctggt t                               21

<210> SEQ ID NO 8
<211> LENGTH: 20

-continued

<212> TYPE: DNA
<213> ORGANISM: Artificial Sequence
<220> FEATURE:
<223> OTHER INFORMATION: PRIMER FOR PCR

<400> SEQUENCE: 8
gggacctcac cagcttatcc                    20

CONSTRUCTION OF HIGH EFFICIENCY RETROVIRAL VECTOR FOR GENE THERAPY OF HUNTER SYNDROME

This application claims the benefit of provisional application Ser. No. 60/360,062 filed Feb. 25, 2002.

FIELD OF THE INVENTION

The present invention relates to a retroviral vector containing an iduronate-2-sulfatase (IDS) gene bat without selective marker gene, which is constructed on the backbone of a minimum sized MLV-based retroviral vector, that does not contain any viral coding sequence but can still produce a high viral titer and drive a high level of gene expression.

BACKGROUND OF THE INVENTION

Hunter syndrome is a lethal lysosomal storage disorder caused by the deficiency of iduronate-2-sulfatase (IDS) and characterized by severe skeletal and neurological symptoms.

Hunter syndrome, {mucopolysaccharidosis (MPS) type II}, results from a defect in the gene encoding the iduronate-2-sulfatase (IDS) (EC 3.1.6.13), which hydrolyzes 2-sulfate groups from nonreducing terminal iduronide moieties of glycosaminoglycan (GAG) molecules (Neufeld E F, *J Biol Chem* 264: 10927–10930, 1989; Hopwood J J and Morris C P, *Mol Biol Med* 7: 381–404 1990; Whitley C B et al., *Hum Mutat* 2: 235–237, 1993). The defect is generally due to point mutations or deletions in the 24 Kb-long gene, mapped on Xq28.2 (Le Guern E et al., *Genomitcs* 1990; 7: 358–362). The disorder clinically manifests as coarse facial features, skeletal deformities (dysostosis multiplex) with short stature and related physical disability, joint contractures, hepatosplenomegaly, and cardiopulmonary deterioration. In severe cases, children experience progressive mental retardation and die before the age of 15. Patients with relatively mild forms have normal intellect, but typically succumb to cardiac and respiratory disease in early adulthood (Young I D and Harper P S, *Hum Genet* 60: 391–392, 1982; Young I D and Harper P S., *Dev Med Child Neurol* 25: 481–489, 1983).

At present, there is no fundamental effective method for treating for Hunter syndrome. Bone marrow transplantation (BMT) has been suggested as one possible therapeutic method.

Previous attempts at systemic therapy were based upon in vitro observations showing the restoration of normal GAG catabolism when IDS-deficient fibroblasts are cocultured with cells having normal enzyme activity (Fratantoni J C et al, *Science* 162: 570–572, 1968). Similar results were obtained from coculturing with normal lymphocytes or macrophages (Olsen I, et al., *Nature* 291: 244–247, 1981; Olsen I et al.,*J Cell Sci* 55: 211–231, 1982; Dean M F et al., *J Cell Sci* 79: 137–149, 1985; Di Natale P et al., *Biochim Biophys Acta* 1138: 143–148, 1992). Such studies provided important insights into the fact that most lysosomal enzymes can be transferred to other cells not only by mannose-6-phosphate (M6P) receptor-mediated endocytosis (Neufeld E F., *Annu Rev Biochem* 60: 257–280, 1991), but also by direct cell-to-cell contact (Olsen I et al., *Nature* 291: 244–247, 1981) Some clinical trials involving BMT have demonstrated therapeutic responses in relevant tissues (Warkentin P I et al., *Birth Defects Orig Artic Ser* 22: 31-391986; Resnick J M et al., *Bone Marrow Transplant* 10: 273–280, 1992), suggesting its clinical potential for lysosomal storage diseases.

However, the application of BMT has been limited by the lack of histocompatible donors, its complications, graft-versus-host disease, and the morbidity and mortality rate of the procedure. Recently, affected blood cells were metabolically corrected with retroviral vectors expressing normal IDS enzyme in vitro (Braun S E et al., *Proc Natl Acad Sci USA* 90: 11830–11834, 1993; Braun S E et al., *Hum Gene Ther* 7: 283–290, 1996). A phase I clinical trial was carried out in one patient using a retoviral vector (Whitley C B et al., *Hum Gene Ther* 7: 537–549, 1996). Accordingly, gene therapy involving the transfer of normal IDS gene to a patient's autologous bone marrow stem cells has been suggested as an alternative method to the conventional BMT. The key to the success of this gene transfer technology is to develop a safe and efficient gene delivery vehicle.

The present inventors previously reported the construction of retroviral vectors with improved safety, gene expression and versatility (U.S. Pat. No. 6,451,595; Kim S H et al., *J Virol* 72: 994–1004, 1998; Yu S S, et al., *Gene Ther* 7: 797–804, 2000). These new vectors, unlike previously developed ones, contain no viral coding sequences but still manage to produce high viral titer and drive high levels of gene expression in transduced cells. Because these vectors do not have any overlapping sequences with packaging genomes, the possibility of homologous recombination is virtually nil and thus the vectors are expected to be safer than the others currently available.

The present inventors have constructed three types of retroviral vectors that can be used for gene therapy of Hunter syndrome, MT-IDS, MIN-IDS, MIM-IDS, using a minimum sized MLV-based retroviral vector, MT, as a backbone. Among the vectors examined, retroviral vector MT-IDS lacking a selectable marker has been found to give a highest viral titer and leads to a highest level of expression of IDS in transduced cells, and, therefore, it may be advantageously used for gene therapy of Hunter syndrome.

SUMMARY OF THE INVENTION

Accordingly, the primary object of the present invention is to provide a retroviral vector containing an IDS gene but without selective marker gene, constructed using a minimum sized MLV-based retroviral vector which does not contain any viral coding sequences, as a backbone.

Another object of the present invention is to provide a method for treating Hunter syndrome by using a CD4-stem cell which is transduced with the retroviral vector of the present invention.

BRIEF DESCRIPTION OF THE DRAWINGS

The above and other objects and features of the present invention will become apparent from the following description of the invention, when taken in conjunction with the accompanying drawings wherein:

MT is a prototype vector containing no viral coding sequences in its genome. MIN-, MIM, MT-IDS and L-IDS-SN are the retroviral vectors constructed for the expression of human IDS. Arrows indicate the transcriptional start site and direction of transcription. The L-IDS-SN vector contains the 417 bp gag coding sequence but other MT-based vectors contain no viral coding sequences at all. SD indicates the splicing donor. Retroviral vectors and coding sequences were drawn in approximate scale only.

Each dot represents the viral titer of an individual subclone, but in this particular graph, some of the dots overlap. Overall, a minimum of 10 subclones were screened for the viral titer in each of the respective vectors. The graph is shown in log scale.

FIG. 3A-B shows the IDS activity in transduced cells.

FIG. 4A-B shows the IDS mRNA expression levels in transduced cells.

FIG. 5A-B shows the transduction efficiency in transduced cells.

DETAILED DESCRIPTION OF THE INVENTION

The present invention provides a retroviral vector containing an iduronate-2-sulfatase (IDS) gene but without selective marker gene, constructed on, as a backbone, a minimum sized MLV-based retroviral vector which does not contain any viral coding sequences but can still produce a high viral titer and drive a high level of gene expression.

IDS hydrolyzes 2-sulfate groups from nonreducing terminal iduronide moieties of glycosaminoglycan (GAG) molecules and a defect in the IDS gene causes Hunter syndrome characterized by severe skeletal and neurological symptoms.

Figure 1:
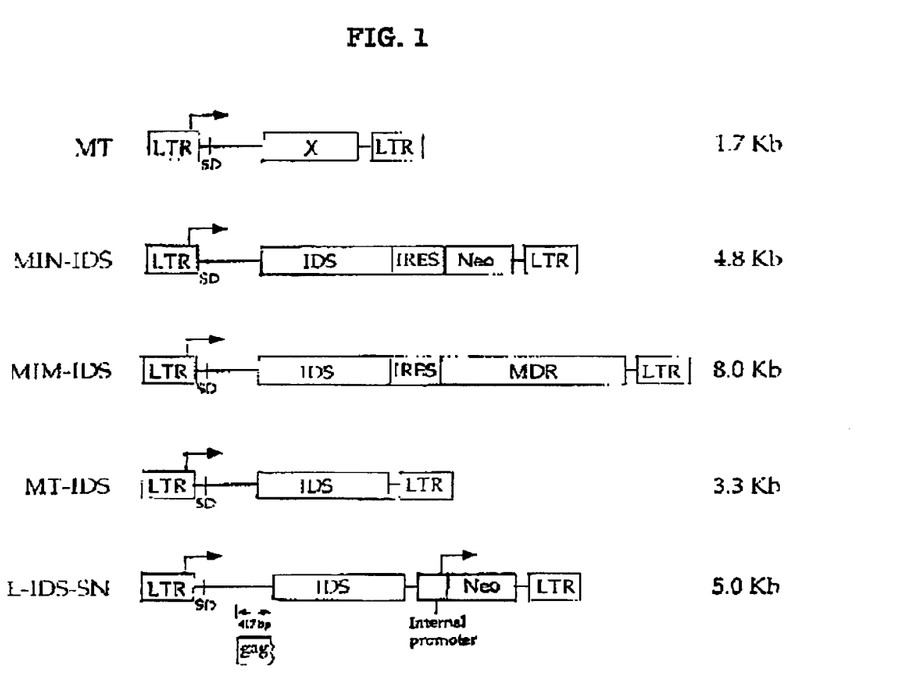
FIG. 1 shows the schematic diagrams of retroviral vectors used in the present invention.

MT is an ideal example of MLV (murine leukemia virus)-based retroviral vector that does not have any viral-coding sequences (FIG. 1)

Specifically, MT retroviral vector comprises nucleotide sequences derived from the original MLV vector which are 5'LTR, the minimal packaging sequence containing the splicing donor at the upstream of the original gag gene, poly-purine track, and 3'LTR;

MT retroviral vector is prepared by deleting IRES-NEO gene from MEN disclosed in U.S. Pat. No. 6,451,595, which is incorporated herein by reference.

The retroviral vector of the present invention contains an IDS gene in the MT retroviral vector (MT-IDS). However, it does not contain any selective marker gene or any other accessory component needed to express the marker gene, such as the internal ribosomal entry site (IRES) or the internal promoter.

Prepared in order to comparatively evaluate the retroviral vector of the present invention are other MT-based retroviral vectors containing IDS gene such as MIN-IDS and MIM-IDS which further comprise a selective marker gene such as bacterial NEO (neomycine resistance) gene and human MDR (multidrug resistance) genes, respectively. MIN is disclosed in FIG. 6 of U.S. Pat. No. 6,451,595 and MIM is constructed by replacing MDR gene in the MIN with NEO gene, whose structure is presented in FIG. 9 of WO 02/20810 under the name of MTM. MDR of human origin is expected to be less immunogenic than the bacterial Neo protein.

As a packaging line of the retroviral vectors of the present invention, PG13 derived from NIH3T3 may be used for its ability to express the Env protein from Gibbon ape Leukemia Virus (GaLV), along with the gag-pol protein of MLV. This is because the major target cells of the gene therapy in the present invention are human CD34+ stem cells, while MLV psuedotyped with the GaLV Env protein has shown to efficiently transduce these cells (Miller A D and Rosman G J., *Biotechniques*. 7: 980982, 984–986, 989–990, 1989; Bunnell B A et al., *Proc Natl Acad Sci USA*. 92: 7739–7743, 1995).

When human CD34+ stem cells are used, over 80% of target cells can be transduced with MT-IDS of the present invention. This suggests that MT-IDS having the following features can be highly effective in gene therapy for Hunter syndrome.

First, MT-IDS produces a higher viral titer than any other MT-based retroviral vectors containing an IDS gene. When viral titers from the best producer lines are compared, MT-IDS generates 6-fold more virus than MIN-IDS and MIM-IDS. As the transduction efficiency is determined primarily by viral titer, MT-IDS has a clear advantage over other vectors and this is presumably due to a shorter length of the MT-IDS genome (Byun J et al., Gene Ther 5: 1441–1444, 1998). The genome length of MT-IDS is 1.5 and 4.7 kb shorter than those of MIN-IDS and MIM-IDS, respectively.

Second, MT-IDS also gives a higher level of IDS expression in different assays. For example, in transient transduction assay using a same volume of culture supernatant from respective producer lines, MT-IDS expresses 3 to 10 fold higher levels of IDS activity, depending on the target cells used. Interestingly, even when a same viral titer is used, there shows a significant difference in the level of IDS activity between MT-IDS and other vectors in different genomic surroundings. Because LTRs of MT-IDS, MIN-IDS and MIM-IDS are identical, it can be interpreted that the increased genome length may lead to a decrease in the steady-state levels of viral RNA resulting from an inefficient RNA elongation process or lower RNA stability. Indeed, results from RNA analysis suggest that the steady level of RNA produced from MT-IDS is the highest among various vectors tested in the is present invention. It is thus clear that the shorter length of the vector genome gives clear advantages in the context of gene therapy.

Third, the retroviral vector of the present invention lacks a selectable marker, which does not lead to any disadvantage. A selectable marker has been naturally used for two major reasons: (1) viral titer can be readily determined; and (2) transduced cells can be selected before these genetically engineered cells are restored to the human subject. However, the recently developed technology involving real time genomic DNA or RT PCR allows quantitative determination of viral titer without using a selectable marker. Furthermore, in the present invention, there is no need to select transduced stem cells by using a selective marker since the major target cells are bone marrow-derived CD34+ cells, which differentiate before doing selection effectively takes place.

Lastly, the absence of a selectable marker ensures no immune response or other potential harmful effects that may arise from expression of this non-therapeutic gene.

The present invention also provides CD34+ bone marrow stem cells transduced with the inventive retroviral vector e.g., MT-IDS. The CD34+ bone marrow stem cells can be efficiently transduced under the condition used in gene therapy trial for SCID-X by pre-stimulating stem cells with a mixture of three cytokines including SCF, FL, IL-3, and TPO, and also by employing extracellular matrix components and truncated fibronectin (Hacein-Bey S et al., *Hum Gene Ther* 12: 291–301, 2001). A minimum of 60% of stem cells can be delivered with the exogenous IDS cDNA through three rounds of transduction carried out over 24 hours.

It appears that there is a optimal amount of viral titer or a optimal volume of viral supernatant used to achieve the highest transduction efficiency. 250 $\mu$l of the viral supernatant (with an approximate moi being 6) gives the highest transduction efficiency, but the use of a larger volume results in a significant decrease in the number of transduced cells. It is possible that the culture supernatant may contain undesirable materials generated from the producer line; for example, the shed envelope protein or related materials that may block the cellular receptor or inhibit the interaction between viral and cellular receptors.

The retroviral vector of the present invention is based on a minimum sized retroviral vector that contains no viral coding sequence, but still ensures a high-level gene expression and high viral titer. The absence of any viral coding sequences warrants no homologous recombination with packaging constructs. Furthermore, the inventive vector is significantly smaller than conventional vectors leading to a higher viral titer and a higher level of gene expression. The absence of a selectable marker further ensures that no immune response will be triggered as a result of overexpression of the marker protein such as MDR.

The present invention further provides a composition comprising CD34+ bone marrow stem cells transduced with the inventive retroviral vector e.g., MT-IDS, which may be used as a gene therapy agent for treating Hunter syndrome.

The composition for gene therapy of the present invention may further comprise pharmaceutically acceptable carriers. Any of the conventional procedures in the pharmaceutical field may be used to prepare oral formulations such as tablets, capsules, pills, granules, suspensions and solutions; rejection formulations such as solutions, suspensions, or dried powders that may be mixed with distilled water before injection; locally-applicable formulations such as ointments, creams and lotions; and other formulations.

Carriers generally used in the pharmaceutical field may be employed in the composition of the present invention. For example, orally-administered formulations may include binders, emulsifiers, disintegrating agents, excipients, solubilizing agents, dispersing agents, stabilizing agents, suspending agents, coloring agents or spicery. Injection formulations may comprise preservatives, unagonizing agents, solubilizing agents or stabilizing agents. Preparation for local administration may contain bases, excipients, lubricants or preservatives. Any of the suitable formulations known in the art (Remington's Pharmaceutical Science [the new edition], Mack Publishing Company, Eaton Pa.) may be used in the present invention.

The inventive composition can be clinically administered as various oral and parenteral formulations. A suitable formulation may be prepared using such excipients as additives, enhancers, binders, wetting agents, disintegrating agents and surfactants, or diluents. Solid formulations for oral administration include pills, tablets, dusting powder, granules and capsules. Those solid formulations may be prepared by mixing one or more excipients, e.g. starch, calcium carbonate, sucrose, lactose and gelatin with dibenzylbuthyllacton lignan derivatives. Also, lubricants such as magnesium stearate and talc may be included in the present formulation. Liquid formulations for oral administration include suspension, solution, emulsion and syrup. Those formulations may contain wetting agents, sweeteners, aromatics and preservatives, in addition to general simple diluents such as water and liquid paraffin. Formulations for parenteral administration include sterilized aqueous solution, suspension, emulsion, freeze-dried alternative treatment and suppositories. Water-insoluble excipients and suspending agents comprise vegetable fats such as propylene glycol, polyethylene glycol and olive oil, and injectable esters such as ethyl oleate. Witepsol®, Macrogol®, Tween® 61, cacao fats, laurin fats and glycerogelatins may be used as bases of suppositories.

The inventive composition may be administered orally or via parenteral routes such as intravenous, intramuscular, subcutaneous, intraabdominal, sternal and arterial injection or infusion, or topically through rectal, intranasal, inhalational or intraocular administration.

It should be understood that the typical daily dose of composition of the present invention ought to be determined in light of various relevant factors including the conditions to be treated, the chosen route of administration, the age, sex and body weight of the individual patient, and the severity of the patient's symptom, and can be administrated in a single dose or in divided dose. Therefore, the daily dose should not be construed as a limitation to the scope of the invention in any way.

The present invention further provides a method for treating Hunter syndrome which comprises subjecting a patient to gene therapy using CD34+ stem cells transduced with the inventive retroviral vector e.g., MT-IDS.

The following Examples are intended to further illustrate the present invention without limiting its scope.

EXAMPLE 1

Construction of Retroviral Vectors

MT, a minimum sized MLV-based vector that contains no viral coding sequences was used as a starting material for constructing the retroviral vector, MT-IDS, of the present invention (FIG. 1). MT retroviral vector was prepared by deleting IRES-NEO gene from MIN vector through the action of BamHI and XhoI and the procedures for preparing MIN are described in U.S. Pat. No. 6,451,595 in detail.

As a control, MIN-IDS (which expresses both the IDS gene and the bacterial neo gene as a bicistronic message) and MIM-IDS (which expresses both the IDS gene and human multidrug resistance-1 (MDR) gene) were used to generate producer lines. The structure and preparing method of the MIN vector had been previously described (U.S. Pat. No. 6,451,595; Yu S S et al., *Gene Ther* 7: 797–804, 2000). The structure of MIM was identical to MIN except that the IRES-neo cassette was replaced with the IRES-MDR cassette in MIM. Preparing procedures of MIM had been described under the name of MTM in International Patent Publication No. WO02/20810. The MDR gene used in MIM-IDS was amplified from pHAMDRGA (Kioka N et al., *Biochem Biophys Res Commun* 162: 224–231, 1989). Reference vector L-IDS-SN was also constructed and used to generate producer lines. L-IDS-SN was derived form LXSN which expresses the gene of interest from the LTR and the selectable marker from the SV40 internal promoter (Miller et al., *Biotechniques* 7:980–990, 1989). The genome lengths of MIN-IDS, MIM-IDS, MT-IDS, and L-IDS-SN were 4.8, 8.0, 3.3 and 5.0 kb, respectively (FIG. 1).

To construct the retroviral vectors expressing the human IDS, IDS cDNA was cloned from the total RNA of human peripheral blood lymphocytes by RT-PCR. The nucleotide sequences of the primers used in this step were as follows:

```
                                          (SEQ ID NO.1)
   IDS5:    GTC GAC GCT AGC ATG CCG CCA CCC CGG
            SalI    NheI
            ACC GGC CGA GGC CTT (SEQ ID NO.2)
   IDS3:    GCG GCC GCT CAA GGC ATC AAC AAC TGG
            NotI
            AAA AGA TCT CC.
```

Amplified IDS cDNA was initially cloned into a vector, PCRII-blunt (Invitrogen, Carlsbad, Calif., USA) and its nucleotide sequence was confirmed. The SalI-NotI fragment of the IDS cDNA was isolated and filled in by the Klenow fragment, and then inserted into the filled BamHI site of MIN, MIM, MT and the filled HindIII site of LXSN, resulting in MIN-IDS, MIM-IDS, MT-IDS and L-IDS-SN, respectively.

EXAMPLE 2

Construction of Producer Lines

Generation of Producer Lines

To construct producer lines for the retroviral vectors of the present invention, L-IDS-SN, MIN-IDS and MIM-IDS plasmids were transfected into 293T (CRL 1609, American Type Culture Collection, Rockville, Md., USA) cells each with pCA-gp and pCA-env plasmids expressing the gag-pol and amphotropic envy, respectively, using FuGene6 (Roche, Germany) according to the manufacturer's instructions. Cell-free viral supernatants were then taken to transduce the packaging line, PG13 (CRL-10686, American Type Culture Collection, Rockville, Md., USA) seeded on the previous day at $2 \times 10^5$ on a 60 mm dish, that expresses the envelope protein of GaLV.

For subcloning, transduced cells were split into ratios of 1:100, 1:50 and 1:5 onto 100 mm dishes 48 hours after transduction and selected in the presence of G418 (1 mg/ml, for MIN-IDS and L-IDS-SN) or vincristine (25 ng/ml, for MIM-IDS) until visible colonies were formed. 10–20 well-separated healthy colonies were isolated by a ring-cloning method and grown to screen for the release of high titers.

Because MT-IDS has no selective marker, the procedure for making the producer line of MT-IDS was modified as follows. After transduction with 293T viral supernatant, PG13 cells were dispensed into a 96-well cell culture plate at a concentration of 0.3 cell/each well. About 14 days after incubation, 20 clones were chosen and transferred to a 24-well plate containing 1 ml of fresh medium per well. To screen for a high-titer producer line, the level of IDS mRNA was first verified from each clone. Total RNA was prepared from each clone, followed by a one-step RT-PCR reaction using oligonucleotide primers specific for the IDS gone, SEQ ID NO.3; 5'-CCCACAGCCTCCTCTTCC-3' and SEQ ID NO.4: 5'-TCTCCTGCCAGTGAGGAAAGAA-3'. For quantitative analysis, real-time quantitative PCR was employed using the ABI Prism 7700 Sequence Detector (Applied Biosystems). The SYBR Green dye (Applied Biosystems) was used in the PCR reaction. The SYBR Green dye is able to bind only to double stranded DNA, and would incorporate mainly into newly synthesized strands during the primer extension step. The amount of synthesized amplicon would be reflected by the intensity of fluorescence emitted from the bound SYBR Green. A clone showing the lowest $C_T$ value was chosen, the cell-free viral supernatant was harvested from this clone and used for the estimation of viral titer (see, PCT/KR02/00858).

293T (CRL 1609), PG13 (CRL-10686), HT1080 (CCL-121) and K562 (CCL-243) used in Examples of the present invention were purchased from the American Type Culture Collection (Rockville, Md., USA). 293T, PG13 and HT1080 were grown in Dulbecco's modified Eagle's medium (D-MEM) supplemented with 10% fetal bovine serum (Gibco-BRL, Grand Island, N.Y., USA, Cat. 26140) K562 was cultured in RPMI 1640 medium supplemented with 10% fetal bovine serum. Each medium used in Examples of the present invention was supplemented with 120 µg/ml penicillin G (Sigma, St. Louis, Mo., USA, P-3032; 1690 U/mg) and 200 µg/ml streptomycin sulfate (Sigma S-9137; 750 U/mg).

Estimation of Viral Titer

Cell-fee viral supernatants obtained from PG13 producer lines were used to transduce HT1080 (human fibrosarcoma cell line) cells plated at $2.5 \times 10^5$ on a 60 mm dish on the previous day. Serially diluted viral supernatants were added to HT1080 cells in the presence of 8 µg/ml polybrene (Sigma, Co.). The next day, transduced cells were transferred to 100 mm plates and selected in the presence of G418 (in cases of MIN-IDS and L-IDS-SN) or vincristine (in a case of MIM-IDS) until visible colonies were formed. Viral titer was estimated by counting the number of drug-resistant colonies.

In the case of MT-IDS, 2 days after transduction, the genomic DNA of transduced HT1080 cells was prepared and digested with EcoRI. Following fall digestion, the concentration of genomic DNA was measured and the same amount of genomic DNA was subjected to PCR amplification in mixtures containing 12.5 µl of TaqMan universal PCR buffer and 1 µl of each of two oligonucleotide primers (final concentrations of 400 nM) of SEQ ID NO. 5: 5'-GTAACGCCATTTTGCAAGGC-3' and SEQ ID NO. 6, 5'-ACCACAAGTCGGATGCAACTG-3'. Reactions were carried out by 45 cycles of denaturation (95° C., 15 seconds), annealing and polymerization steps (60° C., 90 seconds), after a holding step (50° C., 120 s and 95° C., 10 minutes) had been completed. The relative amount of amplified products was analyzed using the ABI Prism 7700 and Sequence Detection System Version 1.6.3. (Applied Biosystems). As calibration standards, two genomic DNAs were prepared: genomic DNA from HT1080 cells transduced with the MIN-IDUA containing neo as a selectable marker at low MOI (<0.1) which was selected with G418; and also genomic DNA from untransduced HT1080 cells. Following digestion with EcoRI, a standard amplification plot was established by mixing the genomic DNA from the transduced HT1080 cell line with that from untransduced HT1080 cells at various ratios. The proportions of cells transduced with varying amounts of MT-IDS were calculated by extrapolating the $C_T$ values from cells transduced to those from standard cells (PCT/KR02/00858; Martell et al., J. Clin. Microbiol. 37:327–332, 1999).

The result showed that roughly 32% amid 52% of the HT1080 cells were transduced by 50 and 100 µl of MT-IDS. Since the number of cells was about $5.0 \times 10^5$, the viral titer of MT-IDS was calculated to be about 4.1 or $3.8 \times 10^6$ cfu/ml. As a control, the viral titer of MIM-IDS was calculated using the above method to be $2.1 \times 10^5$ cfu/ml, which is similar to the result shown in FIG. 2. This confirmed that the viral titer calculated by this new method is comparable to those measured by conventional drug selection procedures.

Figure 2:
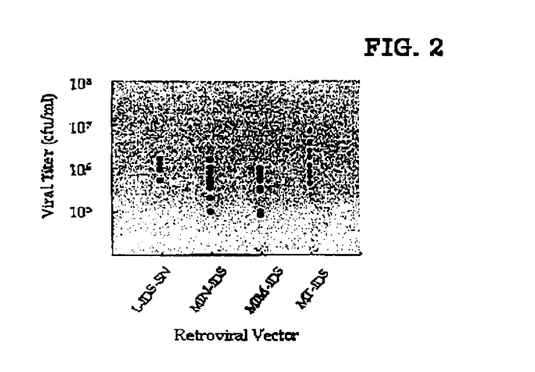
FIG. 2 shows the viral titers of subclones derived from various retroviral vectors.

As shown in FIG. 2, the range of viral titer that could be achieved with MT-IDS was generally higher than those of other vectors, more than 50% of all subcloned producer lines generated higher than $10^6$ viruses per ml. The highest viral titers achieved with MIN-IDS and L-IDS-SN were comparable at approximately $1.5 \times 10^6$ cfu/ml, while MIM-IDS produced a maximum of $8 \times 10^5$ cfu/ml presumably due to the increased length of the genome. MT-IDS always gave the highest viral titer, over $5 \times 10^6$ cfu/ml.

EXAMPLE 3

Level of Gene Expression in Transduced Cells

Figure 3:
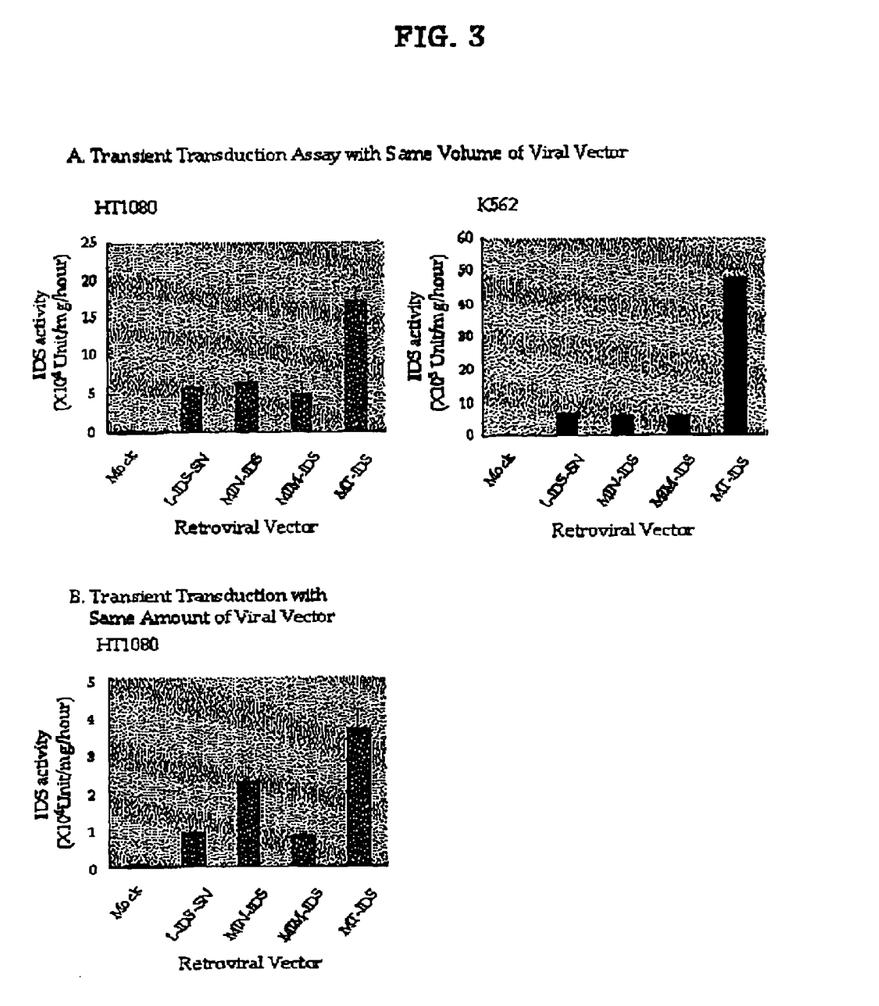

To determine the levels of IDS expression in transduced cells, HT1080 and K562 (human myelogenous cell line) cells were transduced with MT-based vectors and L-IDS-SN in two ways (FIG. 3). In the first transient transduction assay, the same volume of cell-free viral supernatants obtained from respective PG13 producer lines producing the highest viral titer was used to transduce HT1080 cells seeded at $2 \times 10^5$ in a 60 mm dish on the previous day. 1 ml of the viral supernatant was added in the presence of 8 μg/ml polybrene. 2 days following transduction, cells were harvested and assayed for IDS gene expression. For K562 cells, cells were counted and seeded at $1 \times 10^6$ cells/well into 6 well plates. 1 ml of the viral supernatant was added in the presence of polybrene and the plate was centrifuged at 2,800 rpm for 2 hours. After centrifugation, cells were incubated at 37° C. for 2 hours, cells were washed and re-fed with a fresh RPMI 1640 medium supplemented with 10% FBS. Two days following transduction, cells were analyzed for enzyme activity.

IDS assay was performed using the known method (Whitley C B et al., *Hum Gene Ther* 7: 537–549, 1996). Briefly, harvested cells were lysed by five cycles of freezing-thawing. Lysates were dialyzed in dialysis buffer (0.01 M Tris-Cl, pH 7.4, containing 0.01 M sodium chloride) for 18 hours at 4° C. prior to assaying. Protein concentration was measured using the Bradford method. IDS activity was assayed using the radiolabeled disaccharide substrate L-O-(α-iduronic acid-2-sulfate)-(1→4)-D- -2, 5-anhydro[1-$^3$H] mannitol 6-sulfate (Research and Development Limited Partnership, Toronto, Ontario, Canada). An appropriate amount (0.1–10 ug) of cell extract was mixed in 50 μof assay buffer (0.2 M sodium acetate-acetic acid buffer, pH 4.5, containing 10 mM sodium azide) with 50 μl of radioactive substrate (12 nmol/ml) and incubated at 37° C. for 1 hour. Reactions were terminated by adding 1 ml of ice-chilled 1 mM $Na_2HPO_4$ buffer (pH 7.8). An anion-exchange column (Research and Development Limited Partnership, Toronto, Ontario, Canada) was used to remove unreacted substrate from the reaction product. 3 ml of 70 mM sodium formate buffer was added to elute the reaction product. Enzymatic activity was expressed as Unit/mg of proteins. One unit of IDS activity is the amount of enzyme required to catalyze the hydrolysis of 1% $^3$H substrate per hour. The conversion ratio must be maintained so as not to exceed 30% by adjusting the amount of the protein being utilized.

The results are shown in FIG. 3A. The IDS activity in this assay represents the viral titer as well as the level of gene expression driven by the respective retroviral vectors of the present invention. The results show that MT-IDS of the present invention produced 4~10 times higher levels of IDS expression in HT1080 or K562 cells, while the level of IDS activity was comparable among three other vectors (FIG. 3A).

In the second transient transduction assay, the same amount of retroviral vector was used. The retroviral vector from each producer clone was diluted to $5.0 \times 10^5$ and used to transduce $5.0 \times 10^5$ of the HT1080 cells. Two days after transduction, cells were analyzed for enzyme activity and the level of IDS mRNA expression by quantitative PCR and RNA blot hybridization.

The above-mentioned IDS activity assay was performed in the same manner as the above and the result is shown in FIG. 3B. MT-IDS gave the highest level of IDS activity, on average 2- and 4- fold higher levels than MIN-IDS and two other vectors, respectively For RNA blot hybridization, total cellular RNAs were prepared from the HT1080 cells transduced with equal amounts of respective retroviral vectors by the guanidine thiocyanate-cesium chloride method. The DNA probe used for hybridization was the EcoRI HindIII IDS gene fragment of MT-IDS. As a control for variation in the amount of RNA loaded, the same filter was hybridized with the EcoRI fragment of actin cDNA. The total RNA (10 μg) was subjected to 1% formaldehyde-agarose gel electrophoresis, blotted to nitrocellulose membrane (Hybond-C; Amersham, RPN303W, US), and hybridized with a $^{32}$P-labeled IDS probe. The same blots were then hybridized again using a $^{32}$P-labeled cellular actin probe. The experimental variation between the intensities of samples was corrected by dividing the intensity of each sample by the that of the respective actin. Then, the relative intensity was calculated by dividing each intensity by that of MIM-IDS (FIG. 4A).

For quantitative analysis, real-time quantitative PCR was employed using the ABI Prism 7700 Sequence Detector (Applied Biosystems). Total RNA was prepared from the HT1080 cells transduced with equal amounts of respective retroviral vectors and 500 ng of total RNA was used in a one-step RT-PCR reaction using the same primers employed in selecting the MT-IDS producer line (SEQ ID NOs. 3 and 4), wherein the SYBR Green dye was used. A similar system utilizing a separate primer set was designed and run for, β-actin along with every unknown sample to correct for total RNA content.

Figure 4:
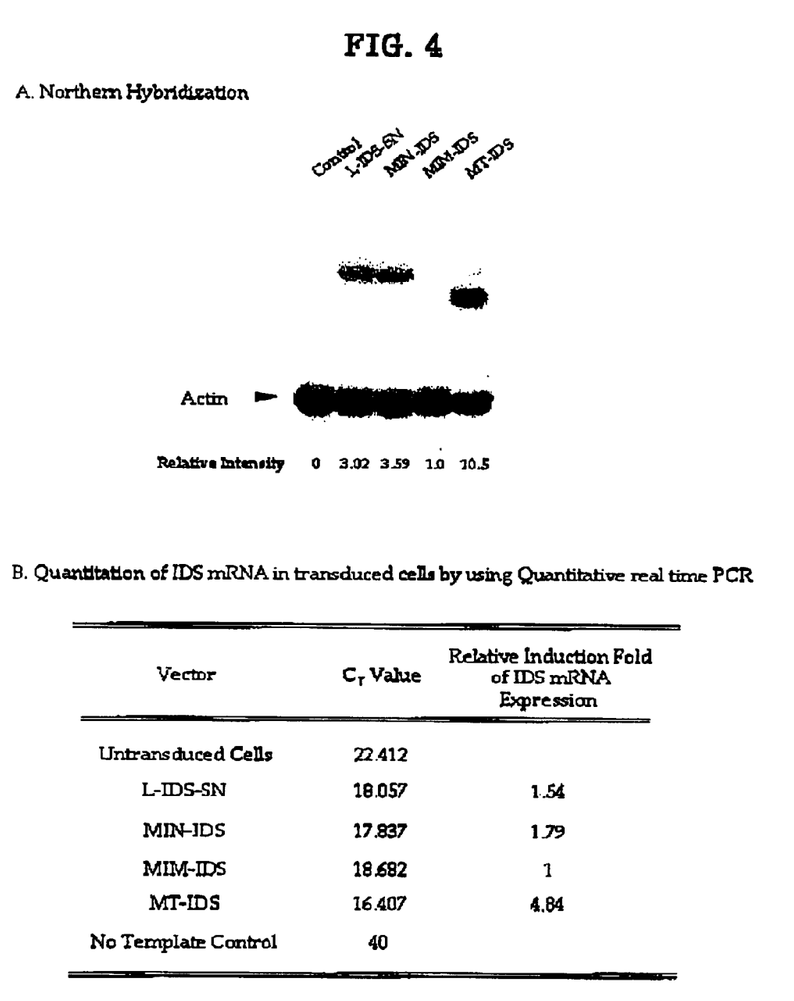

In the RNA blot analysis, the LN vector and all MT-based vectors produced one RNA band of expected size (FIG. 4A). Consistent with the above protein data, MT-IDS produced a minimum 3 fold higher level of IDS-specific RNAs than L-IDS-SN or MIN-IDS, while the amount of RNA generated from MIM-IDS was almost 10 fold lower than that from MT-IDS. A similar observation was made utilizing the real time quantitative RT-PCR method by using a primer pair specific to the IDS cDNA sequence (SEQ ID NOs. 3 and 4). In this analysis, the $C_T$ value would represent the relative amounts of IDS mRNA. MT-IDS showed a 1.4 to 2.3 cycle lower $C_T$ value than other vectors. This means that MT-IDS produced approximately 2.7 to 4.8 fold larger amounts of IDS mRNA than other vectors. Data from these experiments confirm that MT-IDS produced a higher steady-state level of RNA.

Therefore, in this assay, the level of IDS activity represents only the IDS expression level driven by the LTR under a given structure. Again, MT-IDS gave the highest level of IDS activity, on average 2- and 4-fold higher levels than MIN-IDS and two other vectors, respectively (FIG. 3B). These results suggests that the same LTR could give varying results when placed under different genomic environments.

EXAMPLE 4

Characterization of MT-IDS Producer Line Using Human CD34+ Bone Marrow Stem Cells Human CD34+ stem cells were purchased from Takara Shuzo (Shiga, Japan). Cells were pre-stimulated by culturing in X-vivo10 medium (BioWhittaker, Walkersville, N.J.) containing 4% fetal calf serum (Gibco-BRL) in the presence of various cytokine combinations at 37° C., 5% $CO_2$ over 48 hours. The human recombinant cytokines used were SCF (300 ng/ml; R&D Systems, Minneapolis, Minn., USA), Flt-3 ligand (300 ng/ml; R&D Systems), IL-3 (20 ng/ml; R&D Systems) and TPO (100 ng/ml; R&D Systems). The cells were then transduced with the various amounts of viral supernatant (50–1000 ul) on human recombinant CH-296 fibronectin-coated plates (100 μg/well in 6 well plates; fibronectin; kindly provided by Takara Shuzo) (Dao MA, et al., *Blood* 92: 4612–4621, 1998). Viral supernatant was preloaded onto fibronectin-coated well plates 1 hour before applying the prestimulated CD34+ stem cells. After mixing the viral supernatant with 1.5×10⁵ stem cells, the cells were incubated at 37° C., 5% $CO_2$ for 2 hours. After washing the cells with fresh X-vivo10 media, the transduction procedure was repeated two more times over a period of 2 days. Finally, cells were incubated at 37° C., 5% $CO_2$ for 48 hours. After 48 hours, a small fraction of cells were used in a CFC (colony forming cell) assay, while the remaining cells were employed in the PCR analysis.

The transduction efficiency was determined by measuring the frequency of proviral integration by PCR analysis using oligonucleotide primers specific to the downstream region from exon 1 sequences of the IDS gene and to the upstream region from exon 2 sequences. Transduced CD34+ stem cells were lysed at a concentration of 1.5×10⁶ cells/ml by the addition of a solution of nonionic detergent IGEPAL-CA670 (0.45%; Sigma) and Tween 20 (0.45%; Sigma) with proteinase K (60 µg/ml), 50 mM KCl, 10 mM Tris-HCl (pH 8.3) and 2.5 mM $MgCl_2$ (Pan D et al., *Mol Genet Metab* 70: 170–178, 2000). Lysate mixtures were incubated (56° C., 1 hour), followed by a proteinase inactivation (95° C., 20 min). DNA sequences were then amplified by PCR using 25 µl of stem cell lysate as a template and 25 µl of Expand High Fidelity systems (Roche, Germany) containing two nucleotide primers (each at a final concentration of 200 nM) of SEQ ID NO. 7: 5'-CTTCTCTGGCTGGGTCTGGTT-3' and SEQ ID NO. 8: 5'-GGGACCTCACCAGCTTATCC-3'. Reactions were submitted to 30 cycles of denaturation (94° C., 1 min), annealing (60C°, 1 min), and extension (72° C., 90 seconds). This primer pair produced a 0.95 Kb and 0.15 Kb DNA fragment from the endogenous genomic and exogenously added IDS cDNA, respectively. Products amplified from the genomic sequence (0.95 kb) and provirus (0.15 kb) were distinguished by electrophoresis on a 2% agarose gel stained with ethidium bromide. To estimate the transduction efficiency, calibration standards were prepared by using genomic DNAs prepared by mixing at various ratios two kinds of lymphoblastoid cell lines (LCL-LXSN for genomic standard, and LCL-L2SN for proviral standard containing a single copy of the IDS cDNA) (Pan D et al., *Mol Genet Metab* 70: 170–178, 2000). The intensity of the 015 Kb DNA band escalated with the increase in the amount of cells containing IDS cDNA. The intensity of the cDNA band from stem cells transduced with MT-IDS was stronger than that from cells containing a single copy of the IDS cDNA. This suggests that almost all stem cells were transduced with MT-IDS or that more than a single copy of the IDS cDNA was delivered to a single cell (FIG. 5A).

To evaluate the frequency of the transduction, CFC assay was also carried out. In the CFC assay, the transduced cells were counted, and 300 cells and 900 cells were respectively added to 1 ml of semisolid methylcellulose medium (Gibco-BRL; Stem Pro complete methylcellulose medium, Cat. No. 10708-014 and StemCell Technologies; MethoCult G F H4434) in duplicate and then plated. Two weeks later, various kinds of colony forming units (CFU-GEMM, BFU-E, CFU-GM and CFU-E) were formed in methylcellulose media, and individual CFU-GM colonies were picked and analyzed by PCR using the same primers described above. Picked colonies were resuspended in 20 µl of lysis buffer, incubated (56° C., 1 hour) and heat-inactivated (95° C., 20 min). 5 µ7l of lysate was applied in a PCR reaction and used as a template. The conditions for amplification were the same as above except that the reactions consisted of 40 cycles. Amplified products were subjected to a 2% agarose gel stained with ethidium bromide.

Figure 5:
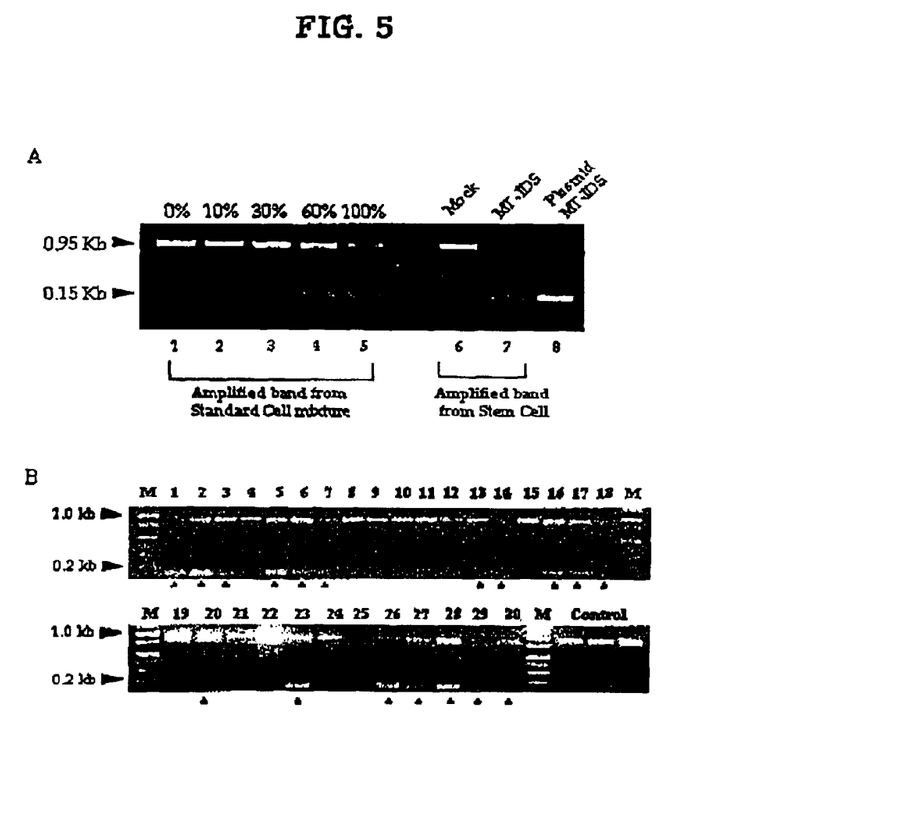

As shown in FIG. 5B, among 30 isolated colonies, the 0.15 Kb band was amplified in 18 colonies. This result shows that around 60% of the colonies were transduced with MT-IDS.

In an effort to uncover the optimum transduction condition, various volumes of the viral supernatant were used to transduce CD34+ stem cells. The stem cells were prestimulated as described previously, and then transduced with 50, 250, 500 and 1000 µl of the supernatant volume of MT-IDS three times over 2 days. Transduced cells were plated in methylcellulose media. Cells transduced with 2504 µl of MT-IDS reproducibly showed a transduction efficiency, of over 80% (Table 1), the highest volume ever observed. This suggests that there is an optimal volume of the viral supernatant or viral titer for the transduction of CD34+ cells.

TABLE I

Effect of Viral Titer in Transduction Efficiencies of MT-IDS in Human CD34+ Bone Marrow Stem cells

| Used Volume of MT-IDS(µl) | Mock | 50 | 250 | 500 | 1000 |
| --- | --- | --- | --- | --- | --- |
| MOI | 0 | 1 | 6 | 12 | 24 |
| Number of Analyzed CFU-GM colonies | 20 | 15 | 31 | 32 | 63 |
| Number of CFU-GM Colonies containing IDS transgene | 0 | 11 | 27 | 16 | 37 |
| Transduction Efficiency (%) | 0 | 73.3 | 87.1 | 50 | 58.8 |

As disclosed and demonstrated above, the present invention provides an efficient retoviral vector which can be advantageously used for gene therapy of Hunter syndrome.

While the invention has been described with respect to the above specific embodiments, it should be recognized that various modifications and changes may be made to the invention by those skilled in the art which also fall within the scope of the invention as defined by the appended claims.

What is claimed is:

1. A recombinant retroviral vector MT-IDS comprising an iduronate 2-sulfatase (IDS) gene and the backbone of a minimum sized murine leukemia virus (MLV)-based retroviral vector containing no selective marker gene, wherein the minimum sized MLV-based retroviral vector comprises 5' LTR (long terminal repeat), the minimal packaging sequence containing the splicing donor at the upstream of the original gag gene, a polypurine track and 3' LTR in order, and which is deposited under Accession NO: KCCM-10550.

* * * * *